US012089899B2

United States Patent
Annoni et al.

(10) Patent No.: US 12,089,899 B2
(45) Date of Patent: Sep. 17, 2024

(54) AUGMENTED AND VIRTUAL REALITY FOR USE WITH NEUROMODULATION THERAPY

(71) Applicant: Boston Scientific Neuromodulation Corporation, Valencia, CA (US)

(72) Inventors: Elizabeth M. Annoni, White Bear Lake, MN (US); Bryan A. Clark, Forest Lake, MN (US); Dennis Zottola, Ventura, CA (US); Kyle H. Srivastava, Saint Paul, MN (US); Jonathan B. Shute, Minnetonka, MN (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 18/068,984

(22) Filed: Dec. 20, 2022

(65) Prior Publication Data
US 2023/0121855 A1 Apr. 20, 2023

Related U.S. Application Data

(63) Continuation of application No. 16/443,562, filed on Jun. 17, 2019, now Pat. No. 11,559,355.
(Continued)

(51) Int. Cl.
*A61B 34/10* (2016.01)
*A61N 1/36* (2006.01)
(Continued)

(52) U.S. Cl.
CPC .......... *A61B 34/10* (2016.02); *A61N 1/36062* (2017.08); *A61B 5/0075* (2013.01);
(Continued)

(58) Field of Classification Search
CPC ......... A61B 34/10; A61B 5/11; A61B 5/0075; A61B 5/1468; A61B 5/318; A61B 5/369;
(Continued)

(56) References Cited

U.S. PATENT DOCUMENTS

5,720,619 A 2/1998 Fisslinger
6,057,846 A 5/2000 Sever, Jr.
(Continued)

*Primary Examiner* — Catherine M Voorhees
(74) *Attorney, Agent, or Firm* — Lewis & Reese, PLLC (57) ABSTRACT

A virtual or augmented reality system is disclosed which is capable of both (i) evaluating prospective implantable neurostimulator patient candidates, and (ii) determining optimal stimulation settings for already-implanted neurostimulation patients. Physiological sensors are included with the system to provide objective measurements relevant to a patient's symptoms, such as pain in a Spinal Cord Stimulation (SCS) system. Such objective measurements are determined during the presentation of various virtual or augmented environments, and can be useful to determining which patients are suitable candidates to consider for implantation. Stimulation settings for already-implanted patients may be adjusted while presenting a virtual or augmented environment to the patient, with objective measurements being determined for each stimulation setting. Such objective measurements can then be used to determine optimal stimulation settings for the patient.

15 Claims, 6 Drawing Sheets

Related U.S. Application Data (60) Provisional application No. 62/711,734, filed on Jul. 30, 2018.

(51) Int. Cl.
    *A61B 5/00*         (2006.01)
    *A61B 5/11*         (2006.01)
    *A61B 5/1468*     (2006.01)
    *A61B 5/318*      (2021.01)
    *A61B 5/369*      (2021.01)

(52) U.S. Cl.
    CPC ............... *A61B 5/11* (2013.01); *A61B 5/1468* (2013.01); *A61B 5/318* (2021.01); *A61B 5/369* (2021.01)

(58) Field of Classification Search
    CPC ... A61B 5/6803; A61B 5/4824; A61B 5/4848; A61B 5/01; A61B 5/02416; A61B 2034/2048; A61N 1/36062; A61N 1/36139; G06F 3/015; G06F 3/011; G06F 3/013; G06F 3/0346
    See application file for complete search history.

(56) References Cited

U.S. PATENT DOCUMENTS

| | | |
|---|---|---|
| 6,186,145 B1 | 2/2001 | Brown |
| 6,425,764 B1 | 7/2002 | Lamson |
| 6,513,085 B1 | 1/2003 | Gugel et al. |
| 6,516,227 B1 | 2/2003 | Meadows et al. |
| 6,896,655 B2 | 5/2005 | Patton et al. |
| 7,856,264 B2 | 12/2010 | Firlik et al. |
| 8,308,562 B2 | 11/2012 | Patton |
| 8,335,569 B2 | 12/2012 | Aghassian |
| 8,498,716 B2 | 7/2013 | Chen et al. |
| 8,531,354 B2 | 9/2013 | Woodard |
| 8,585,609 B2 | 11/2013 | Kiderman |
| 8,630,867 B2 | 1/2014 | Yoo |
| 8,725,364 B2 | 5/2014 | Ishibashi et al. |
| 8,764,655 B2 | 7/2014 | Yoo |
| 8,768,453 B2 | 7/2014 | Parramon et al. |
| 9,471,753 B2 | 10/2016 | Kaula et al. |
| 2005/0216243 A1* | 9/2005 | Graham ................ G16H 40/67 703/11 |
| 2009/0271375 A1 | 10/2009 | Hyde et al. |
| 2012/0021394 A1 | 1/2012 | deCharms |
| 2012/0165898 A1* | 6/2012 | Moffitt ............... A61N 1/37247 607/45 |
| 2014/0067005 A1* | 3/2014 | Kaula ................. A61N 1/37247 715/810 |
| 2014/0344740 A1* | 11/2014 | Kaula ................... G16H 50/50 715/771 |
| 2015/0080982 A1 | 3/2015 | Funderburk |
| 2015/0360038 A1* | 12/2015 | Zottola ............... A61N 1/37247 607/45 |
| 2017/0100602 A1 | 4/2017 | Kaula et al. |
| 2018/0011971 A1 | 1/2018 | Yeh |
| 2018/0085055 A1 | 3/2018 | Annoni et al. |
| 2018/0085584 A1* | 3/2018 | Thakur .............. A61N 1/36139 |
| 2018/0110464 A1 | 4/2018 | Annoni et al. |
| 2018/0154156 A1* | 6/2018 | Clark ................ A61N 1/36175 |
| 2020/0254259 A1 | 8/2020 | Libbus et al. |

\* cited by examiner

AUGMENTED AND VIRTUAL REALITY FOR USE WITH NEUROMODULATION THERAPY

CROSS REFERENCE TO RELATED APPLICATIONS

This is a continuation of U.S. patent application Ser. No. 16/443,562, filed Jun. 17, 2019, which is a non-provisional application of U.S. Provisional Patent Application Ser. No. 62/711,734, filed Jul. 30, 2018. Priority is claimed to these applications, and they are incorporated herein by reference in their entireties.

FIELD OF THE TECHNOLOGY

The present application is related to techniques to improve patient selectivity and the effectiveness of therapy provided by neurostimulation devices.

INTRODUCTION

Implantable stimulation devices are devices that generate and deliver electrical stimuli to nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the techniques within a Spinal Cord Stimulation (SCS) system, such as that disclosed in U.S. Pat. No. 6,516,227. However, the described techniques may find applicability in any implantable medical device system, including a Deep Brain Stimulation (DBS) system.

Figure 1:
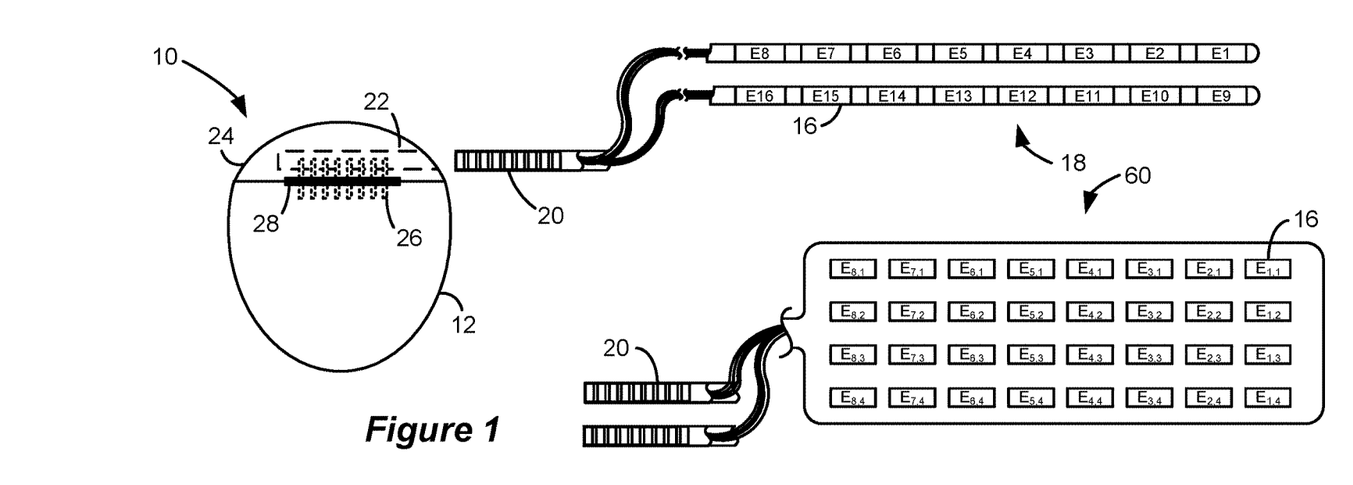
FIG. 1 shows an implantable pulse generator (IPG) and different types of leads that are connectable to the IPG in accordance with an example of the disclosure.

As shown in FIG. 1, a traditional SCS system includes an implantable neurostimulator such as an Implantable Pulse Generator (IPG) 10 (or implantable medical device, more generally), which includes a biocompatible device case 12 formed of titanium, for example. The case 12 typically holds the circuitry and battery 14 (FIG. 2) necessary for the IPG 10 to function, which battery 14 may be either rechargeable or primary in nature. The IPG 10 delivers electrical stimulation to a patient's nerves and tissues through electrodes 16, which, in a SCS system are typically implantable within the epidural space within a patient's spinal column. Common electrode arrangements include a linear arrangement along a percutaneous lead 18 and a two-dimensional arrangement on a paddle lead 60. The proximal ends of the leads 18 and 60 include lead connectors 20 that are connectable to the IPG 10 at one or more connector blocks 22 fixed in a header 24, which can comprise an epoxy, for example. Contacts in the connector blocks 22 make contact with electrode terminals in the lead connectors 20, and communicate with the circuitry inside the case 12 via feedthrough pins 26 passing through a hermetic feedthrough 28 to allow such circuitry to provide stimulation to or monitor the various electrodes 16. The number and arrangement of electrodes on a percutaneous lead 18 or a paddle lead 60 can vary. When percutaneous leads 18 are employed, it is common for two such leads 18 to be implanted with one each on the right and left side of the spinal cord.

Figure 2:
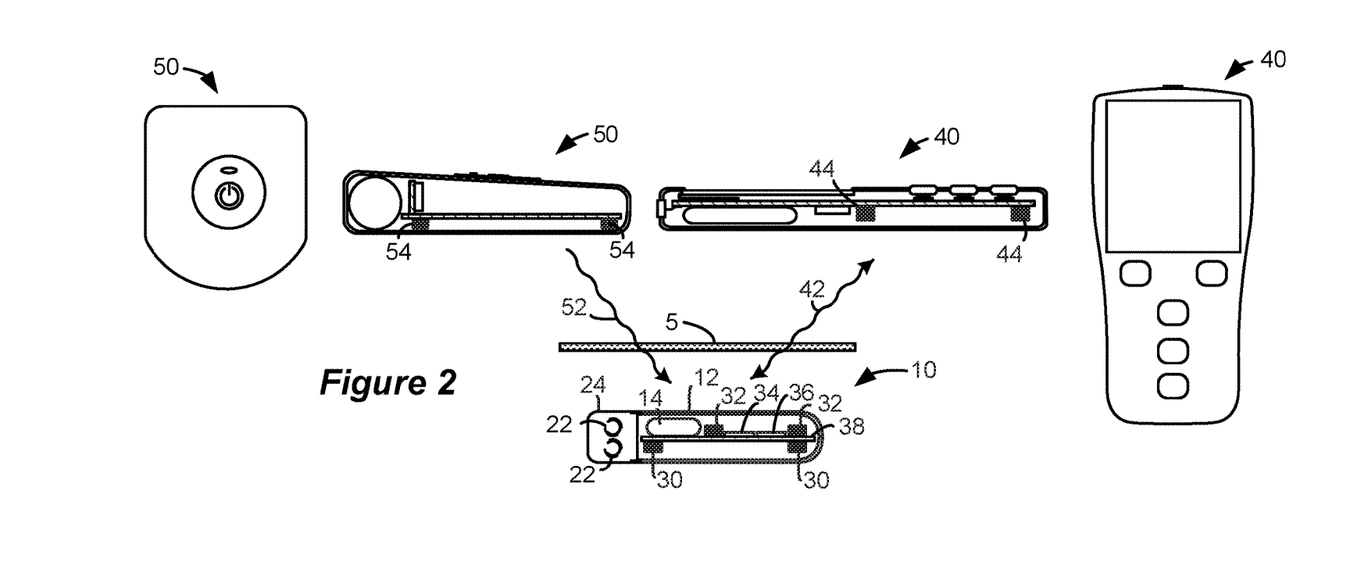
FIG. 2 shows a cross section of the IPG of FIG. 1 as implanted in a patient, as well as external devices that support the IPG, including an external charger and external controller in accordance with an example of the disclosure.

As shown in FIG. 2, IPG 10 contains a charging coil 30 for wireless charging of the IPG's battery 14 using an external charger 50, assuming that battery 14 is a rechargeable battery. If IPG 10 has a non-rechargeable (primary) battery 14, charging coil 30 in the IPG 10 and the external charger 50 can be eliminated. IPG 10 also contains a telemetry coil antenna 32 for wirelessly communicating data with an external controller device 40, which is explained further below. In other examples, antenna 32 can comprise a short-range RF antenna such as a slot, patch, or wire antenna. IPG 10 also contains control circuitry such as a microcontroller 34, and one or more Application Specific Integrated Circuit (ASICs) 36, which can be as described for example in U.S. Pat. No. 8,768,453. ASIC(s) 36 can include stimulation circuitry for providing stimulation pulses at one or more of the electrodes 16 and may also include telemetry modulation and demodulation circuitry for enabling bidirectional wireless communications at antenna 32, battery charging and protection circuitry coupleable to charging coil 30, DC-blocking capacitors in each of the current paths proceeding to the electrodes 16, etc. Components within the case 12 are integrated via a printed circuit board (PCB) 38.

FIG. 2 further shows the external devices referenced above, which may be used to communicate with the IPG 10, in plan and cross section views. External controller (or, remote controller) 40 may be used to control and monitor the IPG 10 via a bidirectional wireless communication link 42 passing through a patient's tissue 5. For example, the external controller 40 may be used to provide or adjust a stimulation program for the IPG 10 to execute that provides stimulation to the patient. The stimulation program may specify an electrode configuration that includes a number of stimulation parameters, such as which electrodes are selected for stimulation; whether such active electrodes are to act as anodes or cathodes; and the amplitude (e.g., current), frequency, and duration of stimulation at the active electrodes, assuming such stimulation comprises stimulation pulses as is typical.

Communication on link 42 can occur via magnetic inductive coupling between a coil antenna 44 in the external controller 40 and the IPG 10's telemetry coil 32 as is well known. Typically, the magnetic field comprising link 42 is modulated, for example via Frequency Shift Keying (FSK) or the like, to encode transmitted data. For example, data telemetry via FSK can occur around a center frequency of $f_c = 125$ kHz, with a 129 kHz signal representing transmission of a logic '1' bit and a 121 kHz signal representing a logic '0' bit. However, transcutaneous communications on link 42 need not be by magnetic induction, and may comprise short-range RF telemetry (e.g., Bluetooth, WiFi, Zigbee, MICS, etc.) if antennas 44 and 32 and their associated communication circuitry are so configured. The external controller 40 is generally similar to a cell phone and includes a hand-holdable, portable housing.

External charger 50 provides power to recharge the IPG's battery 14 should that battery be rechargeable. Such power transfer occurs by energizing a charging coil 54 in the external charger 50, which produces a magnetic field comprising transcutaneous link 52, which may occur with a different frequency ($f_2 = 80$ kHz) than data communications on link 42. This magnetic field 52 energizes the charging coil 30 in the IPG 10, which is rectified, filtered, and used to recharge the battery 14. Link 52, like link 42, can be bidirectional to allow the IPG 10 to report status information back to the external charger 50, such as by using Load Shift Keying as is well-known. For example, once circuitry in the IPG 10 detects that the battery 14 is fully charged, it can cause charging coil 30 to signal that fact back to the external charger 50 so that charging can cease. Like the external controller 40, external charger 50 generally comprises a hand-holdable and portable housing.

External controller 40 and external charger 50 are described in further detail in U.S. Patent Application Publication 2015/0080982. Note also that the external controller 40 and external charger 50 can be partially or fully integrated into a single external system, such as disclosed in U.S. Pat. Nos. 8,335,569 and 8,498,716.

SUMMARY

A method for assessing the suitability of a candidate patient for neurostimulation therapy is disclosed, which may comprise: presenting from a computer device one or more virtual environments to the candidate patient; receiving at the computer device one or more physiological measurements taken from the candidate patient in response to each one of the one or more virtual environments; and determining at the computer device a composite response score based on the one or more physiological measurements; wherein the composite response score is useful for determining whether the candidate patient is a suitable candidate for neurostimulation therapy.

Determining the composite response score may comprise determining a virtual environment response score for each virtual environment using the one or more physiological measurements taken from the candidate patient in response to that virtual environment, and using the virtual environment response scores to determine the composite response score.

The virtual environment may be presented to the candidate patient using a headset or using a virtual reality room.

The method may further comprise determining at the computer device whether the candidate patient is a suitable candidate for neurostimulation therapy based on the composite response score. Determining at the computer device whether the candidate patient is a suitable candidate for neurostimulation therapy may comprise comparing the composite response score to a threshold.

The one or more physiological measurements may be taken from the candidate patient using one or more physiological sensors associated with the patient. The one or more physiological sensors may comprise one or more of a heart sensor, a blood pressure sensor, a galvanic skin response sensor, a respiration rate sensor, an electrocardiogram sensor, a chemical sensor, a neurological sensor, an eye sensor, a temperature sensor, or a motion sensor.

At least one of the one or more virtual environments may comprise an image of a person performing an activity. At least one of the one or more virtual environments may also comprise an image of a neurostimulator implant procedure. At least one of the one or more virtual environments may still further comprise an image indicative of pain in a person. At least one of the one or more virtual environments further may also comprise an image of neurostimulation therapy being applied to the person and a decrease of the pain in the image indicative of pain in the person. At least one of the one or more virtual environments may also comprises an image relevant to a physiological condition of the candidate patient. At least one of the one or more virtual environments may comprise an image designed to elicit a movement response from the candidate patient.

The neurostimulation therapy may comprise spinal cord stimulation therapy. The computing device may comprise a clinician programmer configured to communicate with a neurostimulator device.

A non-transitory computer readable media including instruction executable on a computer device is disclosed, wherein the instructions when executed may be configured to assess the suitability of a candidate patient for neurostimulation therapy by: presenting from the computer device one or more virtual environments to the candidate patient; receiving at the computer device one or more physiological measurements taken from the candidate patient in response to each one of the one or more virtual environments; and determining at the computer device a composite response score based on the one or more physiological measurements; wherein the composite response score is useful for determining whether the candidate patient is a suitable candidate for neurostimulation therapy. The non-transitory computer readable media may also include instructions consistent with the method described earlier.

A method for assessing a patient having a neurostimulator is disclosed, which may comprise: communicating from a computer device a plurality of sets of stimulation parameters for execution by the patient's neurostimulator, wherein each of the sets of stimulation parameters is communicated to the patient's neurostimulator at a different time; presenting from the computer device one or more virtual environments to the patient during the execution of each of the sets of stimulation parameters; receiving at the computer device one or more physiological measurements taken from the patient during the execution of each of the sets of stimulation parameters; determining at the computer device a therapeutic efficacy score for each of the sets of stimulation parameters based on the one or more physiological measurements taken from the patient during that set of stimulation parameters; and determining at the computer device a set of stimulation parameters for the patient using the therapeutic efficacy scores.

The one or more virtual environments may be presented to the patient during execution of one of the sets of stimulation parameters is based on that set of stimulation parameters. The one or more virtual environments may be presented to the patient during execution of one of the sets of stimulation parameters is based the one or more physiological measurements received during that set of stimulation parameters. The one or more virtual environments may be presented to the patient during execution of one of the sets of stimulation parameters is based on that set of stimulation parameters and is based on the one or more physiological measurements received during that set of stimulation parameters. The one or more virtual environments presented to the patient during execution of one of the sets of stimulation parameters may comprise an image indicative of pain derived from the one or more physiological measurements received during that set of stimulation parameters.

The virtual environment may be presented to the patient using a headset. The virtual environment may be presented to the using a virtual reality room.

Determining the set of stimulation parameters using the therapeutic efficacy scores may comprise determining the set of stimulation parameters having a best of the therapeutic efficacy scores.

The one or more physiological measurements may be taken from the patient using one or more physiological sensors associated with the patient. The one or more physiological sensors may comprise one or more of a heart sensor, a blood pressure sensor, a galvanic skin response sensor, a respiration rate sensor, an electrocardiogram sensor, a chemical sensor, a neurological sensor, an eye sensor, a temperature sensor, or a motion sensor.

At least one of the one or more virtual environments may comprise an image of a person performing an activity. At least one of the one or more virtual environments may comprise an image designed to elicit a movement response from the candidate patient.

The neurostimulation therapy may comprise spinal cord stimulation therapy. The computing device may comprise a clinician programmer configured to communicate with the patient's neurostimulator.

A non-transitory computer readable media including instruction executable on a computer device is disclosed, wherein the instructions when executed may be configured to assess a patient having a neurostimulator by: communicating from the computer device a plurality of sets of stimulation parameters for execution by the patient's neurostimulator, wherein each of the sets of stimulation parameters is communicated to the patient's neurostimulator at a different time; presenting from the computer device one or more virtual environments to the patient during the execution of each of the sets of stimulation parameters; receiving at the computer device one or more physiological measurements taken from the patient during the execution of each of the sets of stimulation parameters; determining at the computer device a therapeutic efficacy score for each of the sets of stimulation parameters based on the one or more physiological measurements taken from the patient during that set of stimulation parameters; and determining at the computer device a set of stimulation parameters for the patient using the therapeutic efficacy scores. The non-transitory computer readable media may also include instructions consistent with the method described earlier.

DETAILED DESCRIPTION

As mentioned above, the electrical stimulation that the IPG 10 is capable of delivering is highly customizable with respect to selected electrodes, electrode current amplitude and polarity, pulse duration, pulse frequency, etc. Due to uncertainties in the location of electrodes with respect to neural targets, the physiological response of a patient to stimulation patterns, and the nature of the electrical environment within which the electrodes are positioned, it is difficult to determine the stimulation settings that might provide effective stimulation therapy without employing a trial and error approach. Thus, to determine whether the IPG 10 is capable of delivering effective therapy, and, if so, the stimulation settings that define such effective therapy, the patient's response to different stimulation settings is typically evaluated during a trial stimulation phase prior to the permanent implantation of the IPG 10.

During the trial stimulation phase, the distal ends of the lead(s) are implanted within the epidural space along the spinal cord while the proximal ends of the lead(s), including the electrode terminals 20, are ultimately coupled to an external neurostimulator such as external trial stimulator (ETS) 70, which is not implanted in the patient. The ETS 70 essentially mimics operation of the IPG 10 to provide stimulation to the implanted electrodes 16. This allows the effectiveness of stimulation therapy to be verified for the patient, such as whether therapy has alleviated the patient's symptoms (e.g., pain). Trial stimulation using the ETS 70 further allows for the determination of particular stimulation settings that seem promising for the patient to use once the IPG 10 is later implanted into the patient.

Figure 3:
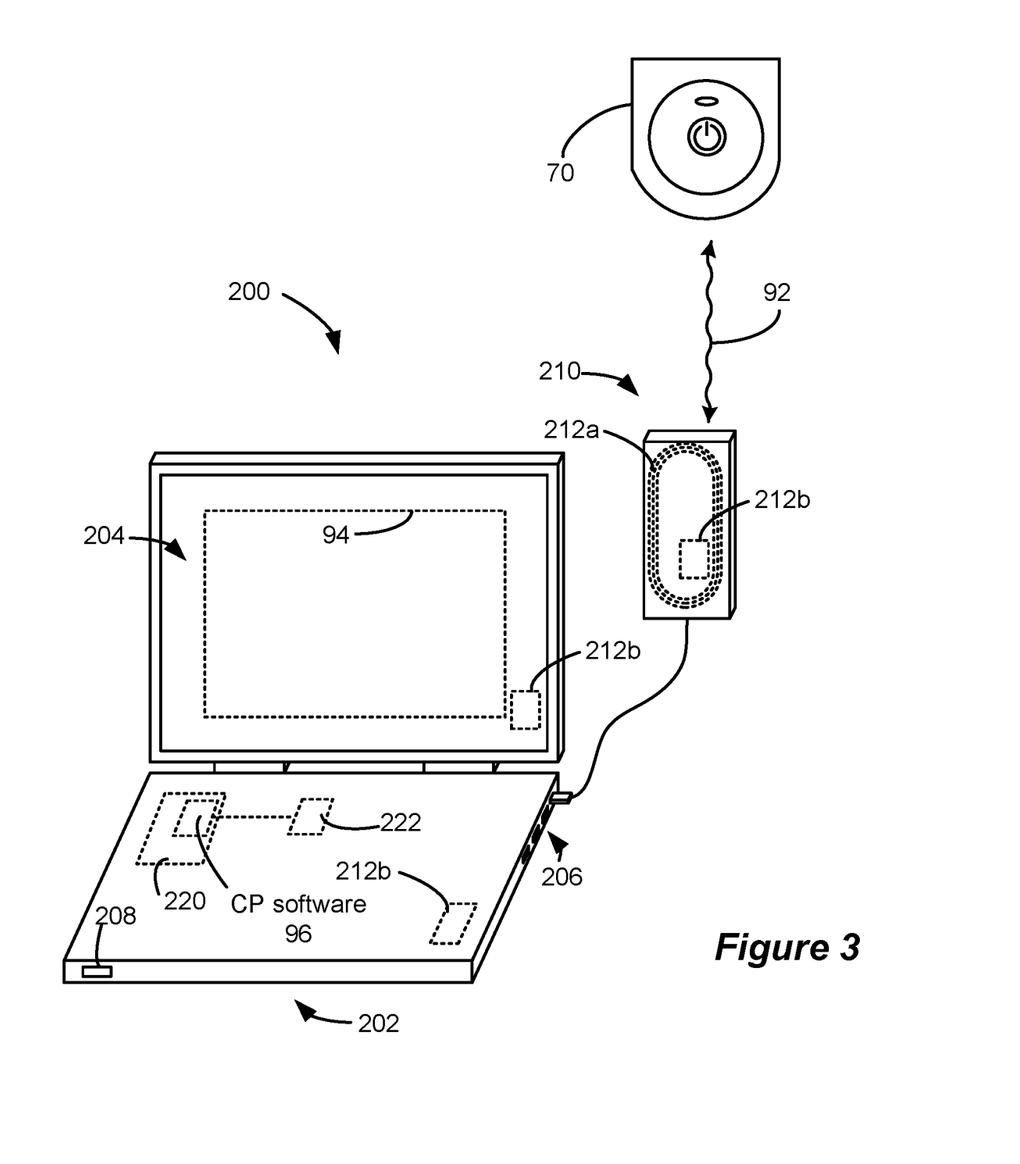
FIG. 3 shows components of a clinician's programmer system, including components for communicating with an external trial stimulator in accordance with an example of the disclosure.

Referring to FIG. 3, the stimulation settings that are executed by the ETS 70 can be provided or adjusted via a wired or wireless link (wireless link 92 shown) from an additional external device known as a clinician's programmer 200, which includes features that enable a clinician to hone in on the appropriate stimulation therapy settings. As shown, CP system 200 can comprise a computing device 202, such as a desktop, laptop, or notebook computer, a tablet, a mobile smart phone, a Personal Data Assistant (PDA)-type mobile computing device, etc. (hereinafter "CP computer"). In FIG. 3, CP computer 202 is shown as a laptop computer that includes typical computer user interface means such as a screen 204, a mouse, a keyboard, speakers, a stylus, a printer, etc., not all of which are shown for convenience. Also shown in FIG. 3 is a communication head 210, which is coupleable to a suitable port on the CP computer 202, such as a USB port 206, for example. While the CP system is shown in communication with the ETS 70, the CP system 200 is also configured to communicate with the IPG 10 once it is implanted.

Communication between the CP system 200 and the ETS 70 or IPG 10 may comprise magnetic inductive or short-range RF telemetry schemes as already described, and in this regard the ETS 70 and the CP computer 202 and/or the communication head 210 (which can be placed proximate to the IPG 10 or ETS 70) may include antennas compliant with the telemetry means chosen. For example, the communication head 210 can include a coil antenna 212a, a short-range RF antenna 212b, or both. The CP computer 202 may also communicate directly with the IPG 10 or the ETS 70, for example using an integral short-range RF antenna 212b.

If the CP system 200 includes a short-range RF antenna (either in CP computer 202 or communication head 210), such antenna can also be used to establish communication between the CP system 200 and other devices, and ultimately to larger communication networks such as the Internet. The CP system 200 can typically also communicate with such other networks via a wired link provided at an Ethernet or network port 208 on the CP computer 202, or with other devices or networks using other wired connections (e.g., at USB ports 206).

To program stimulation parameters, the clinician interfaces with a clinician's programmer graphical user interface (CP GUI) 94 provided on the display 204 of the CP computer 202. As one skilled in the art understands, the CP GUI 94 can be rendered by execution of CP software 96 on the CP computer 202, which software may be stored in the CP computer's non-volatile memory 220. Such non-volatile memory 220 may include one or more non-transitory computer-readable storage mediums including, for example, magnetic disks (fixed, floppy, and removable) and tape, optical media such as CD-ROMs and digital video disks (DVDs), and semiconductor memory devices such as Electrically Programmable Read-Only Memory (EPROM), Electrically Erasable Programmable Read-Only Memory (EEPROM), and USB or thumb drive. One skilled in the art will additionally recognize that execution of the CP software 96 in the CP computer 202 can be facilitated by control circuitry 222 such as a microprocessor, microcomputer, an FPGA, other digital logic structures, etc., which is capable of executing programs in a computing device. Such control circuitry 222 when executing the CP software 96 will in addition to rendering the CP GUI 94 enable communications with the ETS 70 through a suitable antenna 212a or 212b, either in the communication head 210 or the CP computer 202 as explained earlier, so that the clinician can use the CP GUI 94 to communicate the stimulation parameters to the ETS 70.

Prior to the trial stimulation phase, patients are typically evaluated to determine whether they are good candidates for SCS therapy. Such an evaluation may include both physical and psychological aspects. The inventors have observed, however, that despite patient screening, a relatively high proportion of patients do not go forward with full implantation after the trial phase or ultimately terminate therapy after full implantation of the IPG 10. The inventors have further observed that one drawback of existing candidate screening is the subjectivity of the evaluations. Different practitioners may assign different weights to various patient factors and candidate patients, often driven by a desire to be approved for SCS therapy, may exaggerate or understate different factors in hopes of being assessed as a suitable candidate. Thus, there exists a need to improve patient screening to more successfully identify patients that are suitable candidates for SCS therapy.

Disclosed herein is a virtual or augmented reality system that in a first aspect removes some of the subjectivity of patient evaluations for SCS or other neurostimulation therapies. As described below, the system may present a virtual environment to a prospective or current SCS patient that is a wholly simulated environment, or the system may present an augmented environment to the patient that supplements a normal environment that the patient otherwise experiences. For simplicity and for the purpose of this disclosure and the claims, a "virtual" environment, system, reality, or equipment, etc. refers respectively to both virtual and augmented environments, systems, realities, or equipments, etc.

Figure 4:
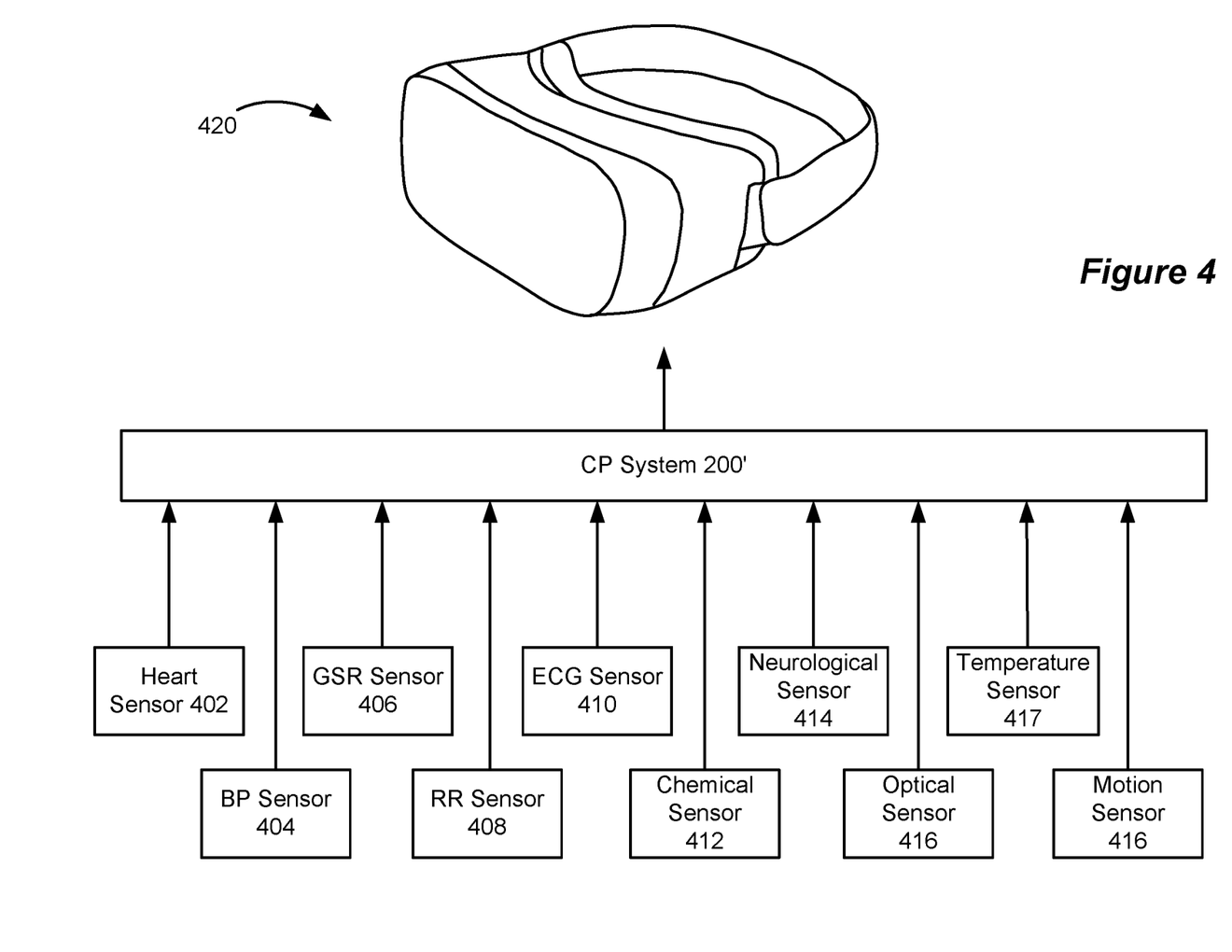
FIG. 4 shows an example of a virtual or augmented reality system in accordance with an example of the disclosure.

As illustrated in FIG. 4, the virtual reality system may include a virtual reality headset 420. As is known, a virtual reality headset 420 fits snugly against the user's face such that the user's only visual perception is that of the virtual reality that is presented via a display inside the headset 420. The headset 420 is connected to an improved CP system 200' via a wired or wireless connection (e.g., via magnetic inductive or short-range RF telemetry schemes as already described). In one embodiment, the improved CP system 200' may include the same functionality and hardware as the CP system 200 described above, but the improved CP system 200' may execute improved CP software 96' to provide various features as described below. While an enclosed headset 420 is shown, the CP system 200' may alternatively be connected to an open headset that enables the user to view their surroundings but that also presents an image via a display to create an augmented reality. One type of such headset is described in U.S. Patent Publication 2015/0360038, which is incorporated herein by reference in its entirety. In yet another embodiment, the CP system 200' may be connected to a large and perhaps curved display that is positioned in a virtual reality room, or to a projector that provides an image to a (curved) wall in a virtual reality room. In such an embodiment, the patient may not wear a headset but may be positioned in the room such that they are immersed in the virtual reality that is presented via the display. Virtual reality images presented to the user by the system can comprise static images, scenes, animations, video, and the like.

Also connected to the improved CP system 200' are a number of patient sensors, again connected via a wired or wireless connection. The sensors can include one or more of a heart sensor 402, a blood pressure sensor 404, a galvanic skin response (GSR) sensor 406, a respiration rate sensor 408, an electrocardiogram (ECG) sensor 410, a chemical sensor 412, a neurological sensor 414, an eye sensor (e.g., camera) 416 for tracking eye movement and/or pupil diameter, a temperature sensor 417, and a motion sensor 418 to monitor movements of the patient's head or other body parts. One or more of the sensors may take the form of a wrist watch that can be worn by the patient, a cuff that is placed around the patient's arm, or other known forms. Other physiological sensors can be used as part of the disclosed system and the sensors illustrated in FIG. 4 are merely examples.

The heart sensor 402 can comprise a heart rate sensor, such as a peripheral pulse sensor. In one example, the heart sensors 402 can detect various activities of the heart, and may provide other data as well. For example, the heart sensor 402 may comprise a pulse oximeter able to describe gas content of the patient's blood. The ECG sensor 410 may comprise multiple leads that are placed at different positions on the patient's body as is known. Such leads may be wired to an ECG monitor (i.e., the ECG sensor 410) that is connected to the CP system 200'. The chemical sensor 412 may comprise a sensor that measures the levels of certain chemicals in the patient's blood or other bodily fluid. For example, the chemical sensor may measure levels of cortisol, which is indicative of the level of stress the patient is experiencing, in the patient's blood. Blood samples may be taken periodically while the patient experiences a virtual reality, and the results may be communicated from the chemical sensor 412 to the CP system 200'. The neurological sensor 414 may include one or more of different types of neurological sensors such as an electroencephalography (EEG) sensor, an electrooculography sensor, and a functional near-infrared spectroscopy (fNIRS) sensor. As is known, each of these types of neurological sensors may include multiple skin-mounted devices (e.g., electrodes) that are wired to the respective sensor 414. In one embodiment, some or all of the skin-mounted devices may be positioned inside the headset 420 such that they are in contact with the patient's skin when the headset 420 is worn. The devices may report measurements back to the respective neurological sensor 414, which may communicate neurological parameters to the CP system 200' while the patient experiences a virtual reality environment. The eye sensor 416 may include one or more cameras and may similarly be mounted on the inside of the headset 420 such that it detects the patient's eyes while the patient experiences the virtual reality environment. Temperature sensor 417 may comprise a sensor to measure a core or peripheral temperature of the patient. The motion sensor 418 for tracking the patient's movements may comprise one or more accelerometers or gyroscopes one or more of which may similarly be mounted to the headset 420 or worn by the patient.

Figure 5:
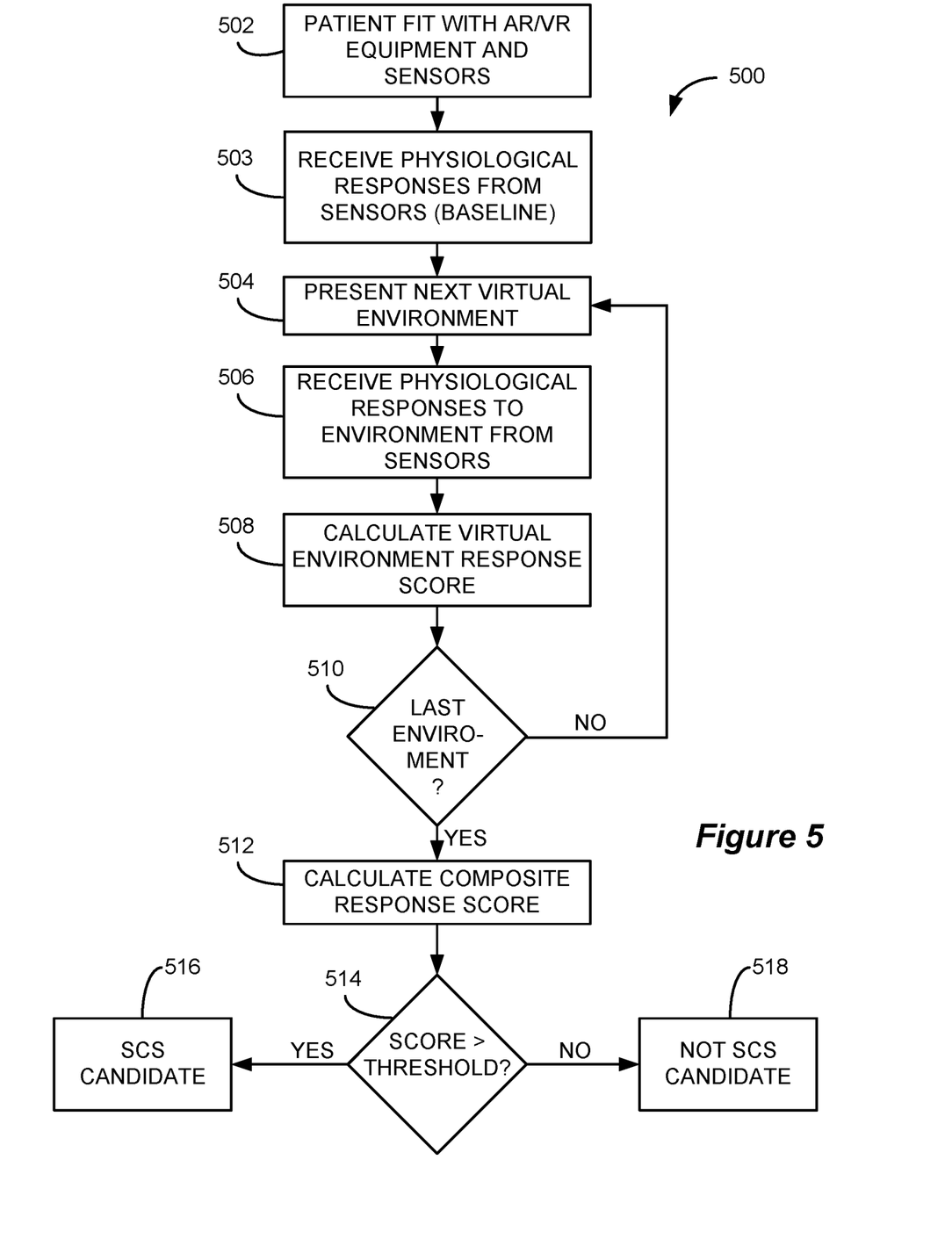
FIG. 5 is a flow chart that shows various aspects of a patient selection process that utilizes a virtual or augmented reality system in accordance with an example of the disclosure.

FIG. 5 illustrates a patient evaluation process 500 preceding implantation that utilizes the virtual reality environment to assess whether a patient is a good candidate to receive SCS therapy. The user is first fit with the virtual reality equipment and one or more patient sensors (502). As described above, the virtual reality equipment may include a VR headset 420, a different type of headset, or a virtual reality room. The patient sensors may include one or more of the patient sensors described above with respect to FIG. 4.

At this point it is optionally useful to measure physiological responses from the sensors and provide such measurements to the CP system 200' (503). This can be useful first to ensure that the sensors are working correctly, and second to establish baseline measurements from the sensors before the patient is exposed to the virtual environment(s) to follow.

After the patient has been fit with the patient sensors and the virtual reality equipment, they are presented one or more virtual environments (504). The virtual environment may be presented via a display that is driven by the CP system 200' (e.g., the headset display or in the virtual reality room).

In one embodiment, the virtual environment may comprise an image that is designed to elicit a response in the patient. For example, the virtual environment may depict a person performing an activity that may cause pain such as lifting a heavy object, climbing stairs, rising from a seated position, etc. The virtual environment may alternatively depict a person performing an activity that is not likely to cause pain such as lying in bed or sitting down. The virtual environment may also depict an SCS implant procedure with the leads and IPG being implanted in an actual or virtual patient. The virtual environment may also present a depiction of pain. For example, the virtual environment may depict an image of pain in a person. In one embodiment, the image of pain may be positioned in a location relative to an image of a person that corresponds to the location at which the patient experiences pain (e.g., the image may appear at the depicted person's lower back if the patient experiences lower back pain). The virtual environment may further depict an image of SCS therapy being applied and, in conjunction, an image that shows the indication of pain decreasing in size. The virtual environment may also depict different types of environments such as a depiction of a person interacting with people, a depiction of the person being dependent upon a caregiver, a depiction of a person being independent as a result of SCS therapy, or a depiction of a person experiencing a type of psychologically stressful event. These types of virtual environments may be designed to evaluate the patient's psychological condition.

Other types of virtual environments may be designed to evaluate the patient's physical condition and elicit a movement response from the patient. These types of environments may prompt the patient to take certain actions. For example, a virtual environment may depict objects moving toward the patient and may prompt the patient to attempt to dodge the objects. Another type of virtual environment may prompt the patient to mimic an activity that is being performed by the person that is depicted in the virtual environment. For example, the virtual environment may prompt the user to mimic a depiction of a person that is standing up, balancing on one leg, kneeling down, bending over at the waist, etc.

In one embodiment, images that are presented in the virtual environment may be actual images of the patient. In another embodiment, the images may be an avatar that is generated to look like the patient. In yet another embodiment, the image may be of a random person or avatar and not related to the particular patient. The particular image that is depicted in the virtual environment may be specifically chosen for the particular patient and may be relevant to a physiological condition of the patient. For example, if the patient experiences pain when rising from a seated position, an image that depicts that activity may be chosen for the patient. In this regard, the CP system 200' may enable a practitioner to control the virtual environment that is being presented. For example, the CP software 96' may provide an interface that enables the practitioner to select an image that is presented as the virtual environment, to determine how long the particular virtual environment is presented, etc.

While the virtual environment is being presented to the patient, the patient's physiological responses to the virtual environment are measured by the one or more patient sensors (the term physiological responses is used here to describe responses received from any of the patient sensors). The physiological responses measured by the sensors are received at the CP system 200' (506). These responses can provide an indication of the patient's anxiety, stress, and pain, for example. The responses can also provide an indication of the patient's physical abilities in response to virtual environments that test such physical abilities (e.g., via motion sensors 418).

Based on the received physiological responses from the sensors, a response score is calculated at the CP system 200' for the virtual environment (508). In one embodiment, the response score may be calculated in accordance with a change in each of one or more physiological parameters from a baseline level (503) to the recorded level during the presentation of the virtual environment. For example, if the patient's heart rate increases from 80 beats per minute to 120 beats per minute in response to presentation of the virtual environment, the response score (at least the portion that is attributable to the heart sensor 402) may be calculated on the basis of the 40 beat per minute increase in the patient's heart rate in response to the virtual environment. As will be understood, the physiological responses that are received at the CP system 200' may be weighted differently. For example, the EEG measurements may be considered to provide a more valuable measure of the patient's response to a virtual environment and so it may be accorded more weight in the calculation of the response score.

After the response score is calculated, it is determined if the virtual environment is the last (or only) one to be presented to the patient (510). If not, a next virtual environment is presented to the patient (504) and the process is repeated. While the response score calculation (508) and next virtual environment presentation (504) are shown as being performed sequentially, this is not specifically necessary. Calculation of the response score for a particular virtual environment can occur during the presentation of a subsequent virtual environment.

If the virtual environment that was presented to the patient is the last virtual environment to be presented, a composite response score is calculated (512). The composite response score is calculated from the response scores associated with each of the virtual environments. In one embodiment, the composite response score may be a sum of the response scores associated with each of the virtual environments that were presented to the patient. In another embodiment, the composite response score is an average of the response scores associated with each of the virtual environments that were presented to the patient. In another embodiment, one or more of the highest and lowest response scores associated with the virtual environments that were presented to the patient may be eliminated and thus not included in the calculation of the composite response score. In yet another embodiment, certain virtual environments may be deemed more relevant and their associated response scores may be given more weight than response scores associated with other virtual environments.

After the composite response score is calculated, it is compared to a threshold score (514). If the calculated composite response score exceeds the threshold, the patient is determined to be a good candidate for SCS therapy (516) and may be progressed to the next round of evaluation (e.g., trial stimulation). If the calculated composite response score is less than the threshold, the patient is determined not to be a good candidate for SCS therapy (518).

As can be understood, the process 500 provides an objective evaluation of a candidate patient's suitability for receiving SCS therapy. Because the process 500 relies upon objective measurements of the candidate patient's response to one or more virtual environments, the subjectivity of current patient evaluation processes is removed and a more accurate assessment of the candidate patient's suitability for therapy can be determined. However, process 500 can also be performed after the patient has been implanted and is receiving SCS therapy. For example, the process 500 may be performed prior to a trial stimulation phase, during a trial stimulation phase, and after permanent implantation of the IPG 10. In such an embodiment, the patient's responses to the virtual environments may be compared to those in a prior evaluation (e.g., prior to a trial stimulation phase) to evaluate the effectiveness of the stimulation therapy that is being provided.

Figure 6:
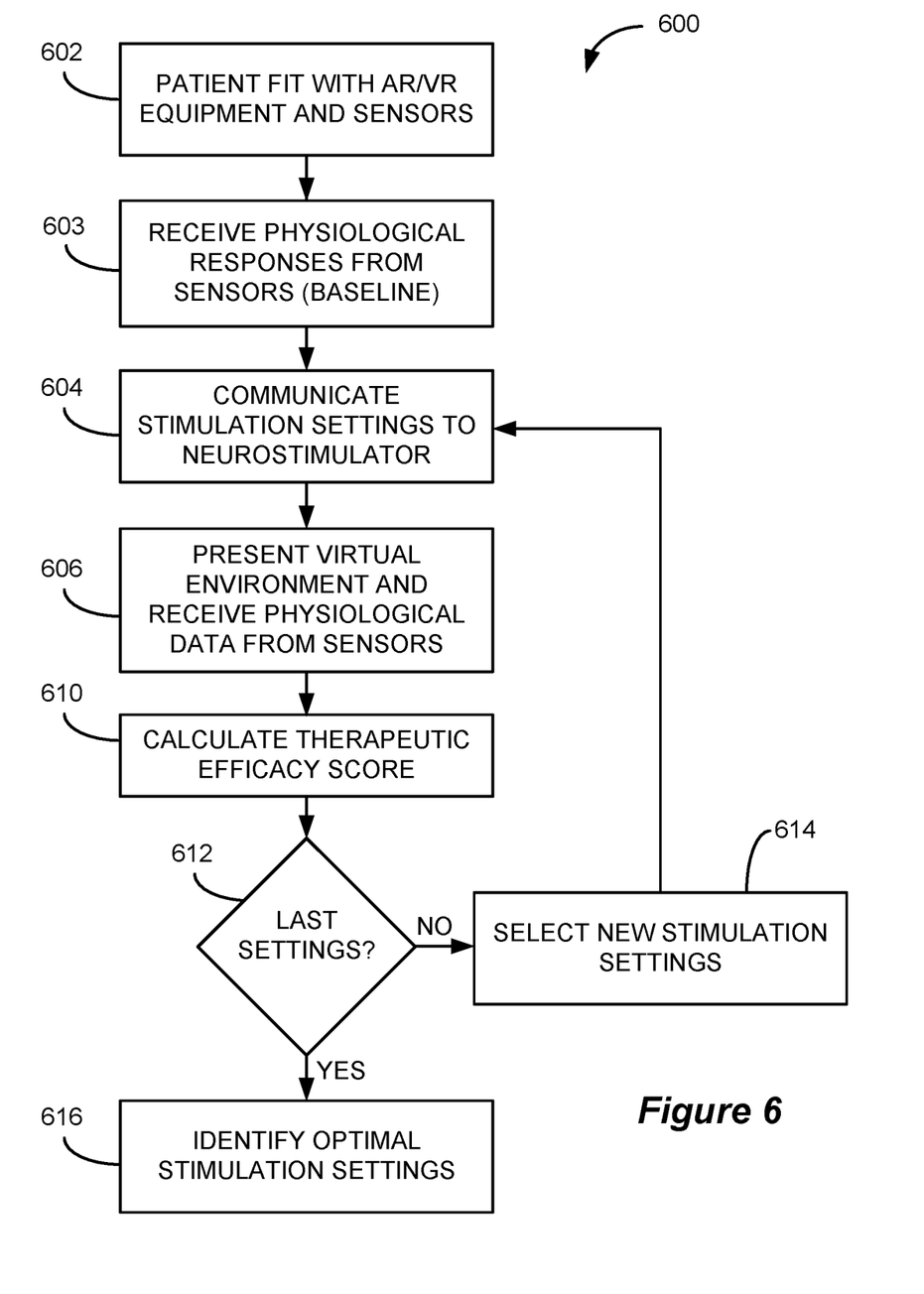
FIG. 6 is a flow chart that shows various aspects of a stimulation evaluation process that utilizes a virtual or augmented reality system in accordance with an example of the disclosure.

FIG. 6 illustrates a stimulation evaluation process 600 that utilizes the virtual reality environment for a patient that has already been implanted, and thus is capable of receiving stimulation delivered via a neurostimulator (i.e., via an ETS 70 during a trial stimulation phase or via an IPG 10 after its permanent implantation). Stimulation evaluation process 600 is useful to choosing optimal stimulation settings for the patient.

Just as with the patient evaluation process 500, the patient is first fit with the virtual reality equipment and the patient sensors (602). At this point it can be useful to receive measurements from the sensors (603) to ensure that they are functioning properly and as a baseline.

Stimulation settings can then be communicated to the patient's neurostimulator via improved CP system 200'. As noted above, the stimulation settings can include various stimulation parameters such as the selected electrodes, electrode current amplitude and polarity, pulse duration, pulse frequency, etc. In one embodiment, the stimulation settings may be manually selected by a practitioner (e.g., via the CP system 200') for the specific patient. In another embodiment, the stimulation parameters may be selected from a group of pre-configured stimulation settings and the process 600 may cycle through different ones of the stimulation settings in the group.

One or more virtual environments are then presented to the patient, and physiological data is received from the sensors at the CP system 200' (606). Just as with the process 500, the virtual environment may be presented via a display that is driven by the CP system 200' (e.g., the headset display or in the virtual reality room).

In one embodiment, the virtual environment is based on the stimulation settings and/or the physiological data. For example, the stimulation settings may be utilized to generate an image of the stimulation that is being provided and the physiological data may be utilized to generate an image of the level of pain that the patient is experiencing. The level of pain that the patient is experiencing may be calculated according to all or a subset of the physiological data from the patient sensors. In one embodiment, these images of pain and stimulation may be presented on an avatar or another image of a person, and the images may be adjusted as the stimulation settings and the physiological data change. In one embodiment, the image of pain may reduce in size whenever stimulation is being provided regardless of the physiological data. Such an embodiment may enable the patient to visualize the effectiveness of the stimulation therapy that is being provided even when the physiological data may not yet reflect a change in the level of pain. The virtual environment may prompt the patient to focus intently on the images of stimulation and pain, and the pain image may be reduced in size as the patient focuses. This again enables the patient to visualize the effectiveness of the stimulation therapy that is being provided.

In one embodiment, the virtual environment may depict an image of a person performing activities such as walking in place, bending from side to side, or squatting down. In such an embodiment, the virtual environment may prompt the patient to mimic the activities that are being performed by the person that is depicted in the virtual environment. The virtual environment may utilize motion sensor data to present an image of the patient's movements as the patient attempts to mimic the activities that are being performed by the person that is depicted in the virtual environment. In one embodiment, the image of the patient's movements may be exaggerated when stimulation is being provided to enable the patient to visualize the effectiveness of the stimulation therapy. The virtual environment(s) presented by the stimulation evaluation process 600 may also comprise the virtual environments presented by the patient evaluation process 500 discussed above.

The presentation of the virtual environment (which may comprise multiple different types of images for each set of stimulation settings) continues for a length of time that enables the collection of a sufficient quantity of physiological data to evaluate the effectiveness of the stimulation settings. The length of time that is required to obtain such a quantity of physiological data may be a user-selectable parameter of the process 600.

For each set of stimulation settings, after a sufficient amount of data has been received from the patient sensors, a therapeutic efficacy score is calculated (610). The therapeutic efficacy score may be based on a pain score that is calculated from the physiological data that is received. More specifically, the therapeutic efficacy score may be determined from a difference between a baseline pain score that is calculated from physiological data that is received when no stimulation is provided (603) and the pain score that is calculated from physiological data that is received when stimulation using the particular stimulation settings is provided. If the current stimulation settings are not the last settings to be evaluated (612), new stimulation settings are selected (614) and communicated to the patient's neurostimulator (604) and the process continues. If the current stimulation settings are the last settings to be evaluated, the optimal stimulation settings are identified (616). In one embodiment, the optimal stimulation settings are the stimulation settings that are associated with the highest therapeutic efficacy score. After the optimal stimulation settings are determined, they may be communicated to the patient's neurostimulator.

As can be understood, the process 600 provides a patient with a visualization of the effectiveness of stimulation therapy and provides an objective measurement of the effectiveness of various stimulation settings. Because the process 600 relies upon objective measurements of the patient's response to different stimulation settings, a more accurate assessment of the effectiveness of different stimulation settings can be determined, and optimal stimulation settings can be determined. In one embodiment, the process 600 may be performed one or more times during a trial stimulation phase or after permanent implantation of the IPG 10. In such an embodiment, the patient's responses to different stimulation settings can be periodically evaluated to ensure that the most optimal stimulation therapy is being provided.

Figure 7:
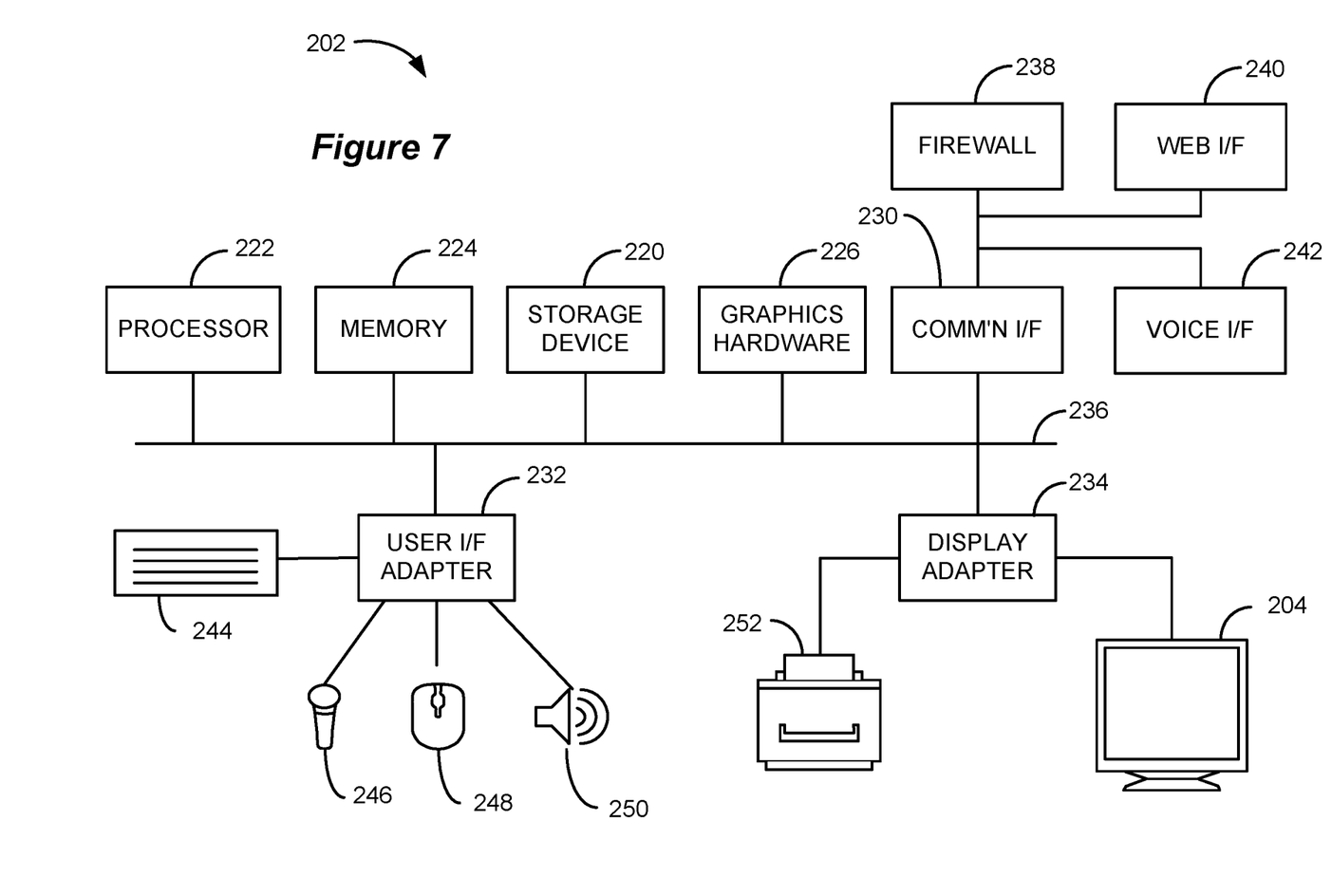
FIG. 7 illustrates a representative computing environment on which software that provides a patient selection process and/or a stimulation evaluation process using a virtual or augmented reality system may be executed in accordance with an aspect of the disclosure.

FIG. 7 illustrates the various components of an example CP computer 202 that may be configured to execute CP software 96', which CP software 96' may include program code that, when executed, provides the functionality of processes 500 and/or 600. The CP computer 202 can include the processor 222, memory 224, storage 220, graphics hardware 226, communication interface 230, user interface adapter 232 and display adapter 234—all of which may be coupled via system bus or backplane 236. Memory 224 may include one or more different types of media (typically solid-state) used by the processor 222 and graphics hardware 226. For example, memory 224 may include memory cache, read-only memory (ROM), and/or random access memory (RAM). Storage 220 may comprise a non-transitory computer readable medium for storing computer program instructions or software (e.g., CP software 96'), including instructions for implementing processes 500 and 600, preference information, device profile information, and any other suitable data. Storage 220 may include one or more non-transitory computer-readable storage mediums including, for example, magnetic disks (fixed, floppy, and removable) and tape, optical media such as CD-ROMs and digital video disks (DVDs), and semiconductor memory devices such as Electrically Programmable Read-Only Memory (EPROM), Electrically Erasable Programmable Read-Only Memory (EEPROM), and USB or thumb drive. Memory 224 and storage 220 may be used to tangibly retain computer program instructions or code organized into one or more modules and written in any desired computer programming language. As will be understood, the CP software 96' may be stored on a medium such as a CD or a USB drive, pre-loaded on a computing device such as the CP computer 202, or made available for download from a program repository via a network connection. Communication interface 230 (which may comprise, for example, the ports 206 or 208) may be used to connect the CP computer 202 to a network. Communications directed to the CP computer 202 may be passed through a protective firewall 238. Such communications may be interpreted via web interface 240 or voice communications interface 242. Illustrative networks include, but are not limited to: a local network such as a USB network; a business' local area network; or a wide area network such as the Internet. User interface adapter 232 may be used to connect a keyboard 244, microphone 246, pointer device 248, speaker 250 and other user interface devices such as a touch-pad and/or a touch screen (not shown). Display adapter 234 may be used to connect display 204 and printer 252. Processor 222 may include any programmable control device. Processor 222 may also be implemented as a custom designed circuit that may be embodied in hardware devices such as application specific integrated circuits (ASICs) and field programmable gate arrays (FPGAs). The CP computer 202 may have resident thereon any desired operating system.

While the above processes 500 and 600 have been described in terms of its performance on a CP computer 202, it will be understood that the processes can also be performed on a different type of device such as a personal electronics device like a phone or tablet, or an external device capable of communicating with an IPG or ETS. Moreover, while the processes 500 and 600 have been described as being implemented as part of CP software 96', it will be understood that the processes 500 and 600 may alternatively be embodied in software that is separate and distinct from the CP software 96. Finally, it should be understood that the steps of processes 500 and 600 can occur in different orders, and that not all illustrated steps are necessary in a useful implementation. Further, additional steps can be added.

While the invention herein disclosed has been described by means of specific embodiments and applications thereof, numerous modifications and variations could be made thereto by those skilled in the art without departing from the scope of the invention set forth in the claims.

What is claimed is:

1. A method for assessing a patient having a neurostimulator, comprising:
   communicating from a computer device a plurality of sets of stimulation parameters for execution by the patient's neurostimulator, wherein each of the sets of stimulation parameters is communicated to the patient's neurostimulator at a different time;
   providing from the computer device one or more virtual environments that are presented to the patient during the execution of each of the sets of stimulation parameters using virtual reality equipment;
   receiving at the computer device one or more physiological measurements taken from the patient during the execution of each of the sets of stimulation parameters;
   determining at the computer device a therapeutic efficacy score for each of the sets of stimulation parameters based on the one or more physiological measurements taken from the patient during each set of stimulation parameters; and
   determining at the computer device a set of stimulation parameters for the patient using the therapeutic efficacy scores.

2. The method of claim 1, wherein the one or more virtual environments presented to the patient during execution of one set of the sets of stimulation parameters is based on that one set of stimulation parameters.

3. The method of claim 1, wherein the one or more virtual environments presented to the patient during execution of one set of the sets of stimulation parameters is based on the one or more physiological measurements received during that one set of stimulation parameters.

4. The method of claim 1, wherein the one or more virtual environments presented to the patient during execution of one set of the sets of stimulation parameters is based on that one set of stimulation parameters and is based on the one or more physiological measurements received during that one set of stimulation parameters.

5. The method of claim 1, wherein the one or more virtual environments presented to the patient during execution of one set of the sets of stimulation parameters comprises an image indicative of pain derived from the one or more physiological measurements received during that one set of stimulation parameters.

6. The method of claim 1, wherein the virtual reality equipment comprises a headset.

7. The method of claim 1, wherein the virtual reality equipment comprises a virtual reality room.

8. The method of claim 1, wherein determining the set of stimulation parameters using the therapeutic efficacy scores comprises determining the set of stimulation parameters having a best of the therapeutic efficacy scores.

9. The method of claim 1, wherein the one or more physiological measurements are taken from the patient using one or more physiological sensors associated with the patient.

10. The method of claim 9, wherein the one or more physiological sensors comprise one or more of a heart sensor, a blood pressure sensor, a galvanic skin response sensor, a respiration rate sensor, an electrocardiogram sensor, a chemical sensor, a neurological sensor, an eye sensor, a temperature sensor, or a motion sensor.

11. The method of claim 1, wherein at least one of the one or more virtual environments comprises an image of a person performing an activity.

12. The method of claim 1, wherein at least one of the one or more virtual environments comprises an image designed to elicit a movement response from the candidate patient.

13. The method of claim 1, wherein the neurostimulation therapy comprises spinal cord stimulation therapy.

14. The method of claim 1, wherein the computing device comprises a clinician programmer configured to communicate with the patient's neurostimulator.

15. A non-transitory computer readable media including instruction executable on a computer device, wherein the instructions when executed are configured to assess a patient having a neurostimulator by:
communicating from the computer device a plurality of sets of stimulation parameters for execution by the patient's neurostimulator, wherein each of the sets of stimulation parameters is communicated to the patient's neurostimulator at a different time;
providing from the computer device one or more virtual environments that are presented to the patient during the execution of each of the sets of stimulation parameters using virtual reality equipment;
receiving at the computer device one or more physiological measurements taken from the patient during the execution of each of the sets of stimulation parameters;
determining at the computer device a therapeutic efficacy score for each of the sets of stimulation parameters based on the one or more physiological measurements taken from the patient during each set of stimulation parameters; and
determining at the computer device a set of stimulation parameters for the patient using the therapeutic efficacy scores.

* * * * *